(12) United States Patent
Nakagawa (10) Patent No.: US 8,998,813 B2
(45) Date of Patent: Apr. 7, 2015

(54) IMAGE FORMING APPARATUS AND IMAGE FORMING METHOD

(75) Inventor: Katsumi Nakagawa, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 285 days.

(21) Appl. No.: 13/496,760

(22) PCT Filed: Nov. 9, 2010

(86) PCT No.: PCT/JP2010/070251
§ 371 (c)(1),
(2), (4) Date: Mar. 16, 2012

(87) PCT Pub. No.: WO2011/062125
PCT Pub. Date: May 26, 2011

(65) Prior Publication Data
US 2012/0179041 A1 Jul. 12, 2012

(30) Foreign Application Priority Data

Nov. 17, 2009 (JP) ................................ 2009-261898
Sep. 2, 2010 (JP) ................................ 2010-196429
Nov. 1, 2010 (JP) ................................ 2010-245390

(51) Int. Cl.
*A61B 8/00* (2006.01)
*A61B 5/00* (2006.01)
(Continued)

(52) U.S. Cl.
CPC ................ *A61B 8/00* (2013.01); *A61B 5/0073* (2013.01); *A61B 5/0095* (2013.01); *A61B 5/7257* (2013.01); *A61B 8/08* (2013.01); *G01S 15/8977* (2013.01); *G01S 15/8993* (2013.01)

(58) Field of Classification Search
USPC .................................. 600/407, 437, 443, 454
See application file for complete search history.

(56) References Cited

U.S. PATENT DOCUMENTS 4,597,292 A * 7/1986 Fujii et al. ........................ 73/599
4,850,366 A * 7/1989 Ito et al. ......................... 600/454
(Continued)

FOREIGN PATENT DOCUMENTS

| CN | 1909836 | 2/2007 |
|---|---|---|
| EP | 42288 | 12/1981 |
| JP | 2005-028166 | 2/2005 |
| WO | 96/04589 | 2/1996 |

OTHER PUBLICATIONS

Office Action issued on Oct. 15, 2013 in counterpart Chinese (PRC) patent application 201080051347.9, with translation.
(Continued)

*Primary Examiner* — Tse Chen
*Assistant Examiner* — Joel F Brutus
(74) *Attorney, Agent, or Firm* — Fitzpatrick, Cella, Harper & Scinto (57) ABSTRACT

An image forming apparatus has acoustic transducers; and an image processing unit which calculates intensity of acoustic waves irradiated from regions inside a subject respectively by processing received signals, which are output from the acoustic transducers, by a Fourier-domain method. The image processing unit includes: a coefficient memory which stores coefficients computed in advance, the coefficient being a value determined only by a position of the acoustic transducer, position of the region and a time of receipt of the acoustic wave; a multiplier unit which multiplies the received signal of the acoustic transducer by the corresponding coefficient; and a voxel memory which accumulates multiplication results of the multiplier unit for each region.

11 Claims, 8 Drawing Sheets (51) Int. Cl.
*A61B 8/08* (2006.01)
*G01S 15/89* (2006.01)

(56) References Cited

U.S. PATENT DOCUMENTS

| | | | |
|---|---|---|---|
| 5,685,308 A | 11/1997 | Wright et al. | 600/443 |
| 6,015,385 A * | 1/2000 | Finger et al. | 600/443 |
| 6,278,890 B1 * | 8/2001 | Chassaing et al. | 600/407 |
| 6,461,298 B1 * | 10/2002 | Fenster et al. | 600/437 |
| 6,567,688 B1 * | 5/2003 | Wang | 600/430 |
| 8,246,544 B2 | 8/2012 | Uchikawa et al. | 600/453 |
| 2004/0006271 A1 * | 1/2004 | Golland et al. | 600/443 |
| 2006/0052697 A1 * | 3/2006 | Hossack et al. | 600/437 |
| 2009/0005685 A1 | 1/2009 | Nagae et al. | 600/459 |

OTHER PUBLICATIONS

P. Burgholzer et al., "Temporal Back-Projection Algorithms for Photoacoustic Tomography with Integrating Line Detectors", *Inverse Problems* 23, pp. S65-S80 (2007).

G. Paltauf et al., "Experimental Evaluation of Reconstruction Algorithms for Limited View Photoacoustic Tomography with Line Detectors", *Inverse Problems* 23, pp. S81-S94 (2007).

M. Xu et al., "Photoacoustic Imaging in Medicine", *Review of Scientific Instruments* 77, 041101 (2006).

Y. Xu et al., "Exact Frequency-Domain Reconstruction for Thermoacoustic Tomography—I. Planar Geometry", *IEEE Transactions on Medical Imaging*, vol. 21, No. 7, pp. 823-828 (Jul. 2002).

Office Action issued on Sep. 24, 2014 in counterpart Japanese patent application 2010-245390, with translation.

* cited by examiner

IMAGE FORMING APPARATUS AND IMAGE FORMING METHOD

TECHNICAL FIELD

The present invention relates to an image forming apparatus and an image forming method for receiving acoustic waves which are generated from a subject, and creating image data of the tissue of each region and characteristics distribution.

BACKGROUND ART

As a technology to generate image data on the interior of a subject using acoustic waves, an ultrasonic echo method and photoacoustic tomography (PAT) method, for example, are known. The ultrasonic echo method is a method for generating image data by transmitting ultrasonic waves to the interior of the subject, and receiving the ultrasonic waves reflected by the tissue inside the subject. The photoacoustic tomography method is a method for generating image data by receiving acoustic waves irradiated from the interior of the subject by the photoacoustic effect. The photoacoustic effect is a phenomenon whereby acoustic waves (typically ultrasonic waves) are generated when such electromagnetic pulses as visible lights, near-infrared lights and microwaves are irradiated onto a subject, and the subject is heated due to the absorption of the electromagnetic waves, and is thermally expanded.

A time-domain method and Fourier-domain method are known as beam forming methods for image forming using the ultrasonic echo method and PAT method. The Fourier-domain method is a method for Fourier-transforming time-series signals so as to transform variables from time to frequency by transforming the spatial coordinates into a wave number, and then performing processing (NPL (Non-Patent Literature) 1). The Fourier-domain method is characterized in high-speed processing by using a fast Fourier transform (FFT). Since CPU speeds have increased, software-based numerical processing has become practical, and because of recent advancements in parallel processing, the future of software-based image processing, that is the Fourier-domain method, is promising. Particularly in a PAT image forming apparatus, it is preferable to use a Fourier-domain method.

[NPL 1] Minghua Xu and Lihong V. Wang: Photoacoustic imaging in biomedicine, Review of Scientific Instruments, Vol. 77, 041101, Apr. 17, 2006

SUMMARY OF INVENTION

Linear type or sector type probes, where acoustic transducers are one-dimensionally arrayed and scanning is electronically performed, are often used in a conventional ultrasonic echo and PAT methods. If these types of probes are used, a two-dimensional image of the cross-section of the subject can be formed. However in order to decrease the occurrence of missing an affected area, obtaining a three-dimensional image is effective. If a three-dimensional image is used, review of the image after diagnosis and confirmation by a third party are easier. For example, in order to obtain a three-dimensional image, a probe, in which acoustic transducers are one-dimensionally arrayed, is mechanically scanned in a direction vertical to the electronic scanning direction, or a probe in which acoustic transducers are two-dimensionally arrayed, is used.

However forming three-dimensional image data makes the data volume to be processed enormous. Especially when a high resolution image is demanded, real-time processing is impossible, which is unacceptable for an operator who is accustomed to operating conventional apparatuses. This situation is more serious in PAT, where image processing is often performed by software, and at the moment, it takes at least several tens of seconds to generate three-dimensional image data, even if a fast Fourier-domain method is used, in other words, more advances are necessary to implement real-time operation.

The present invention provides a technology which enables real-time processing of a high resolution three-dimensional image by increasing the speed of the image data generation processing based on a Fourier-domain method in photoacoustic tomography and ultrasonic echo methods.

The present invention in its first aspect provides an image forming apparatus for creating image data from information on the interior of a subject based on acoustic waves irradiated from the interior of the subject, comprising: a plurality of acoustic transducers which receive acoustic waves and convert the acoustic waves into signals; and an image processing unit which calculates intensity of acoustic waves irradiated from a plurality of regions inside the subject respectively by processing received signals, which are output from the plurality of acoustic transducers, by a Fourier-domain method, wherein the image processing unit includes: a coefficient memory which stores coefficients computed in advance, the coefficient being a value of a term determined only by a position of the acoustic transducer, position of the region and a time of receipt of the acoustic wave (receipt time), in a formula to determine intensity of an acoustic wave irradiated from a region based on the received signals of the plurality of acoustic transducers; a multiplier unit which obtains a coefficient corresponding to the received signal of the acoustic transducer from the coefficient memory, and multiplies the received signal by the coefficient; and a voxel memory which accumulates multiplication results of the multiplier unit for each region.

The present invention in its second aspect provides an image forming method for receiving acoustic waves irradiated from a plurality of regions inside a subject for a predetermined period using a plurality of acoustic transducers, converting the acoustic waves into received signals, and processing the received signals by a Fourier-domain method to create image data of intensity of the acoustic waves irradiated from the regions, comprising the steps of: computing, in advance, a value of a term determined only by a position of the acoustic transducer, position of the region and a time of receipt of the acoustic wave, in a formula to determine intensity of an acoustic wave irradiated from a region based on the received signals of the plurality of acoustic transducers and storing the computed values in a coefficient memory as coefficients; obtaining a coefficient corresponding to the received signal of the acoustic transducer from the coefficient memory, and multiplies the received signal by the coefficient; and accumulating results of multiplying the received signal by the coefficient in a voxel memory for each region.

The present invention in its third aspect provides a non-transitory computer readable medium which stores a program for causing a computer to execute the steps of the above image forming method.

According to the present invention, real-time processing of a high resolution three-dimensional image data becomes possible by increasing the speed of image data generation processing based on a Fourier-domain method in photoacoustic tomography and ultrasonic echo methods.

Further features of the present invention will become apparent from the following description of exemplary embodiments with reference to the attached drawings.

DESCRIPTION OF EMBODIMENTS

Before describing a method of the present invention, an algorithm of generating PAT image data based on the current Fourier-domain method and the problems thereof will be described according to the description of Wang (NPL 1). Wang describes three types of surfaces on which acoustic transducers surrounding a subject are arrayed: spherical surface, plane and cylindrical surface, but here a case of a plane is described to simplify explanation. For convenience of explanation, in some cases symbols which are different from Non-Patent Literature 1 may be used.

Figure 7:
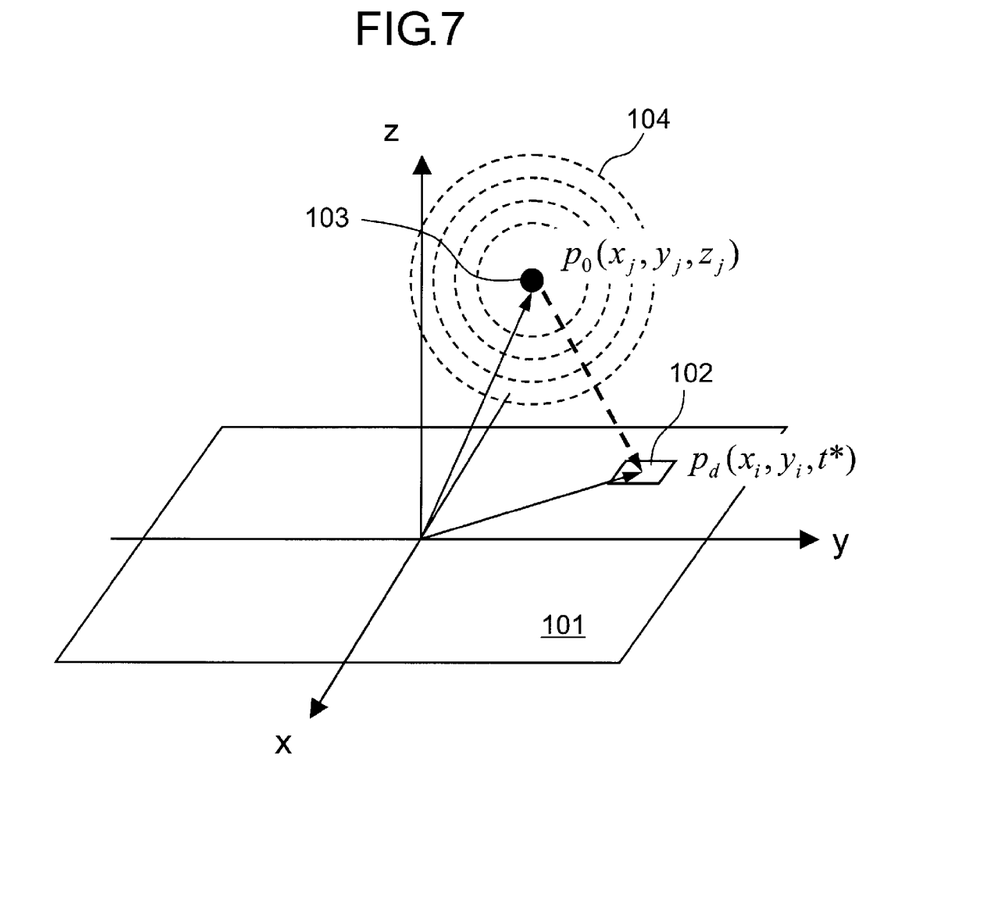
FIG. 7 is a diagram depicting a coordinate system in the description of the principle of a Fourier-domain method.

In FIG. 7, 101 represents a plane on which acoustic transducers are arrayed. The x axis and the y axis included in this plane 101 intersect orthogonally, the z axis is perpendicular to the plane 101, and a subject exists in an area where z is positive with respect to this plane 101. M number of acoustic transducers are arrayed on the plane 101, and N number of regions in the area z>0 are measured. 102 represents the i-th acoustic transducer (i=1, 2, ..., M). 103 represents the j-th region inside the subject (j=1, 2, ..., N). When an electromagnetic pulse is irradiated from various type of pulse lasers and magnetron tubes, and is absorbed by the region j, the region j heats up and expands suddenly, and irradiates acoustic wave 104. It is assumed that the initial pressure of the acoustic wave is $p_0(x_j,y_j,z_j)$. $(x_j,y_j,z_j)$ are coordinates of the j-th region. Although this depends on the size of the region, an acoustic wave generated by irradiating an electromagnetic pulse (called a "photoacoustic wave") is normally an ultrasonic wave of which frequency is about several hundred kHz to several MHz. The photoacoustic wave 104 propagates inside the subject, is received by the i-th acoustic transducer 102, and is output as a received signal $p_d(x_i,y_i,t^*)$. $(x_i,y_i)$ are coordinates of this acoustic transducer 102, and $t^*(=ct)$ is an elapsed time after irradiating an electromagnetic pulse standardized by sound speed c inside the subject. In PAT, in which an electromagnetic pulse cannot be irradiated locally to a specific region inside a subject, $p_d(x_i,y_i,t^*)$ is a value generated by adding photoacoustic waves from a plurality of regions.

Figure 8:
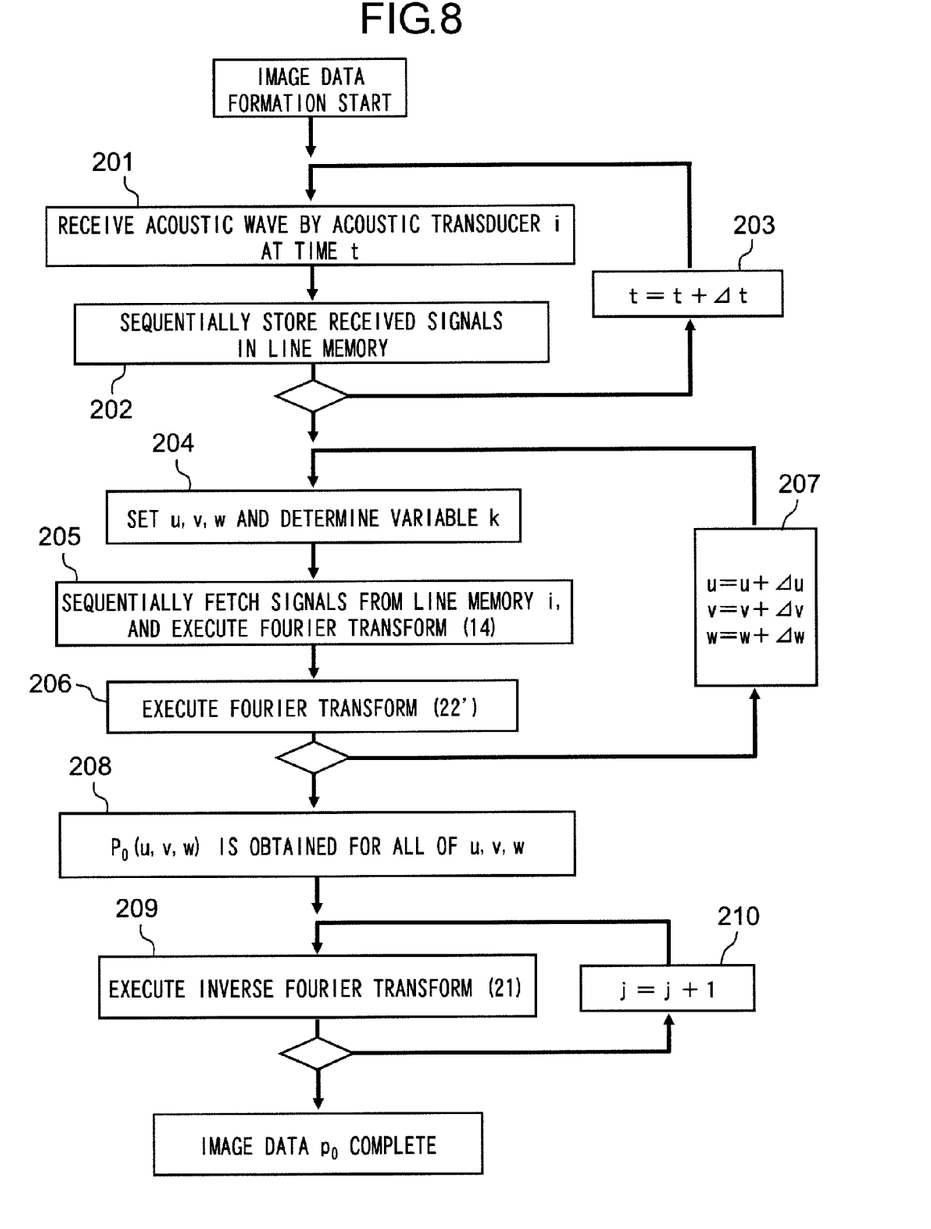
FIG. 8 is a flow chart depicting a conventional computing algorithm of a Fourier-domain method.

An algorithm of a conventional Fourier-domain method will be described for each step with reference to FIG. 8. The equation numbers conform to Non-Patent Literature 1. It is assumed that variables t, u, v, w and j or the like have been initialized before Step 201.

Step 201: Receive photoacoustic waves by M number of acoustic transducers at time t, and output the received signals $p_d(x_i, y_i, t^*)$.

Step 202: Store the received signals in a line memory corresponding to each acoustic transducer. The line memory here refers to a memory normally referred to as FIFO (First In First Out), where time series information is input in the sequence of the series, and is output in the sequence of the input.

Step 203: Repeat the reception and storing to a memory during a predetermined period.

Step 204: Determine three variables (u, v, w) of a Fourier transform having wave number dimensions.

Step 205: Execute the Fourier transform with respect to time using variable k, which is determined by $k=(u^2+v+w^2)^{1/2}$ from the predetermined (u, v, w).

$$P_d(x_i,y_i,k)=\int_{-\infty}^{\infty} p_d(x_i,y_i,t^*)\exp(ikt^*)dt^* \quad (14)$$

Eq. (14) is expressed as an integration of an infinite area, but actually discrete numerical integration is executed in a finite range. Hereafter description on integration which appears herein below shall be interpreted in a same manner. Then, Step 206: Execute the Fourier transform with respect to length.

$$Q(u,v,k)=\iint_{-\infty}^{\infty} P_d(x_i,y_i,k)\exp(iux_i+ivy_i)dx_i dy_i \quad (22')$$

Eq. (22') is shown as inverse Fourier transform (22) in NPL 1, but here, a Fourier transform is used for convenience of explanation. $(x_i, y_i)$ are coordinates of the acoustic transducer i. Eq. (22') is represented as an integration of the infinite region, but is actually computed as the sum of M number of acoustic transducers i.

Steps 207, 208: Execute Steps 205 and 206 for all (u, v, w) sets which are set in advance, then a set of $$P_0(u, v, w) = \frac{2w\,\mathrm{sgn}(w)}{\sqrt{u^2+v^2+w^2}} Q\left[u, v, \mathrm{sgn}(w)\sqrt{u^2+v^2+w^2}\right] \quad (23)$$

is obtained. Here sgn(w) is a function which is 1 when w>0, 0 when w=0, and −1 when w<0.

Step 209: Execute an inverse Fourier transform with respect to (u, v, w) using the obtained set of $P_0(u,v,w)$, as $$p_0(x_j, y_j, z_j) = \frac{1}{(2\pi)^3} \iiint_{-\infty}^{\infty} P_0(u, v, w)\exp(-iux_j - ivy_j - iwz_j)du\,dv\,dw \quad (21)$$

then, the initial pressure $p_0(x_j,y_j,z_j)$ of the region j is determined.

Step 210: Repeat the inverse Fourier transform (21) for N number of regions in the subject, whereby image data of the entire subject is generated.

A number of times of multiplication required for all the above steps is roughly estimated. It is assumed that a number of acoustic transfers is M, a number of regions to be observed in the subject is L in one dimension, that is the total $L^3(=N)$, a number of times of reception of acoustic waves is T, and a number of sets of the three variables (u, v, w) used for the Fourier transform is $F^3$ (F in one dimension). With respect to (u, v, w), a number of times of multiplication required is T in Step 205, M times in Step 206, T×M times if these steps are combined, and T×M×F³ times if this processing is executed for all the sets of (u, v, w). The number of times of multiplication required for (u, v, w) is F³ in Step 209, so if this step is executed for all the regions, L³×F³ times of multiplication is required, totalling (T×M×F+L×F³)=(T×M+L)F³ times. Since setting as F≈L, T≈L, and M≈L² is efficient to maintain accuracy, a number of times of multiplication is approximately 2L⁶ times, and if one multiplication is executed in one step, the number of computing steps is 2L⁶. A fast Fourier transform (FFT) can be applied to (x, y), so this number of steps can be decreased to about L²[L×log(L)]²=L⁴ log²(L), but if L is increased to implement high resolution, the number of steps still become enormous, which makes it difficult to reconstruct an image in real-time.

After concerted study, the present inventor discovered that by transforming the above mentioned algorithm, a part of the processing can be executed in parallel, and total image forming time can be dramatically decreased. Hereafter algorithms used for the image forming apparatus and image forming method of the present invention will be described in detail.

If Eq. (23) is substituted for $P_o(u,v,w)$ of Eq. (21), then $$p_0(x_j, y_j, z_j) = \frac{1}{(2\pi)^3} \int\int\int_{-\infty}^{\infty} \frac{2w\,\mathrm{sgn}(w)}{\sqrt{u^2+v^2+w^2}} Q\left[u, v, \mathrm{sgn}(w)\sqrt{u^2+v^2+w^2}\,\right] \times \exp(-iux_j - ivy_j - iwz_j)dudvdw \quad (101)$$

is established. (A number in the hundreds is a number originally used for this description).

If Eq. (22') is substituted for Q of Eq. (101), then $$p_0(x_j, y_j, z_j) = \frac{1}{(2\pi)^3} \int\int\int_{-\infty}^{\infty} \frac{2w\,\mathrm{sgn}(w)}{\sqrt{u^2+v^2+w^2}} \left[\int\int_{-\infty}^{\infty} P_d\left(x_i, y_i, \mathrm{sgn}(w)\sqrt{u^2+v^2+w^2}\right) \times \exp(iux_i + ivy_i)dx_i dy_i\right] \exp(-iux_j - ivy_j - iwz_j)dudvdw \quad (102)$$

is established.

If Eq. (14) is substituted for $P_d$ of Eq. (102), then $$p_0(x_j,y_j,z_j) = \iiint_{-\infty}^{\infty} A(x_j,y_j,z_j;x_i,y_i,t^*) p_d(x_i,y_i,t^*) dx_i dy_i dt^* \quad (103)$$

is established, where $$A(x_j, y_j, z_j; x_i, y_i, t^*) = \frac{1}{(2\pi)^3}\int\int\int_{-\infty}^{\infty}\frac{2w\,\mathrm{sgn}(w)}{\sqrt{u^2+v^2+w^2}} \exp\left\{i\left[\frac{u(x_i-x_j)+v(y_i-y_j)-wz_j+}{\mathrm{sgn}(w)\sqrt{u^2+v^2+w^2}\,t^*}\right]\right\}dudvdw \quad (104)$$

Eq. (103) is a formula to determine an intensity $p_0$ of an acoustic wave irradiated by region j, based on the received signals of the plurality of acoustic transducers. The term $A(x_j,y_j,z_j;x_i,y_i,t^*)$ in Eq. (103) does not include $p_d(x_i,y_i,t^*)$, as shown in Eq. (104), and integration with respect to (u, v, w) is all completed within this expression. Therefore if the position $(x_i,y_i)$ of the acoustic transducer, position $(x_j,y_j,z_j)$ of a region in the subject, of which image data is generated (or relative position of the acoustic transducer and the region), and arrival time (receipt time) of acoustic waves from all the regions, are known, then coefficient A can be computed in advance using Eq. (104).

(Algorithm 1)

An example of the algorithm for determining initial pressure $p_0(x_j,y_j,z_j)$ with respect to all the regions $(x_j,y_j,z_j)$ (j=0, 1, . . . N) using the obtained coefficient A will be described with reference to FIG. 1. In the following description, a number in ( ) is a number assigned to a composing element of the apparatus shown in FIG. 4, which is described later. In the coefficient memory (408), coefficients A corresponding to all the pre-computed combinations of i,j,t* are stored. It is assumed that the voxel memory (410), variables t, i or the like have been initialized before Step 701.

Figure 1:
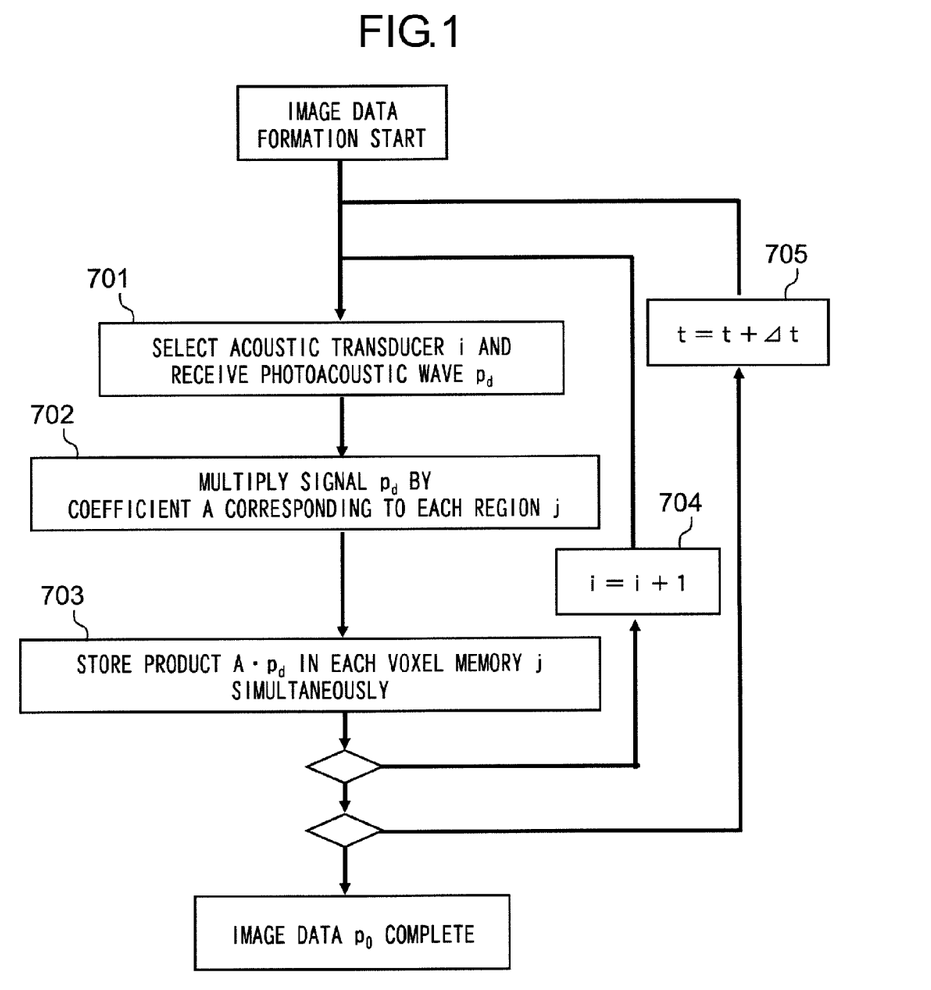
FIG. 1 is a flow chart depicting a computing algorithm 1 of the present invention.
Figure 4:
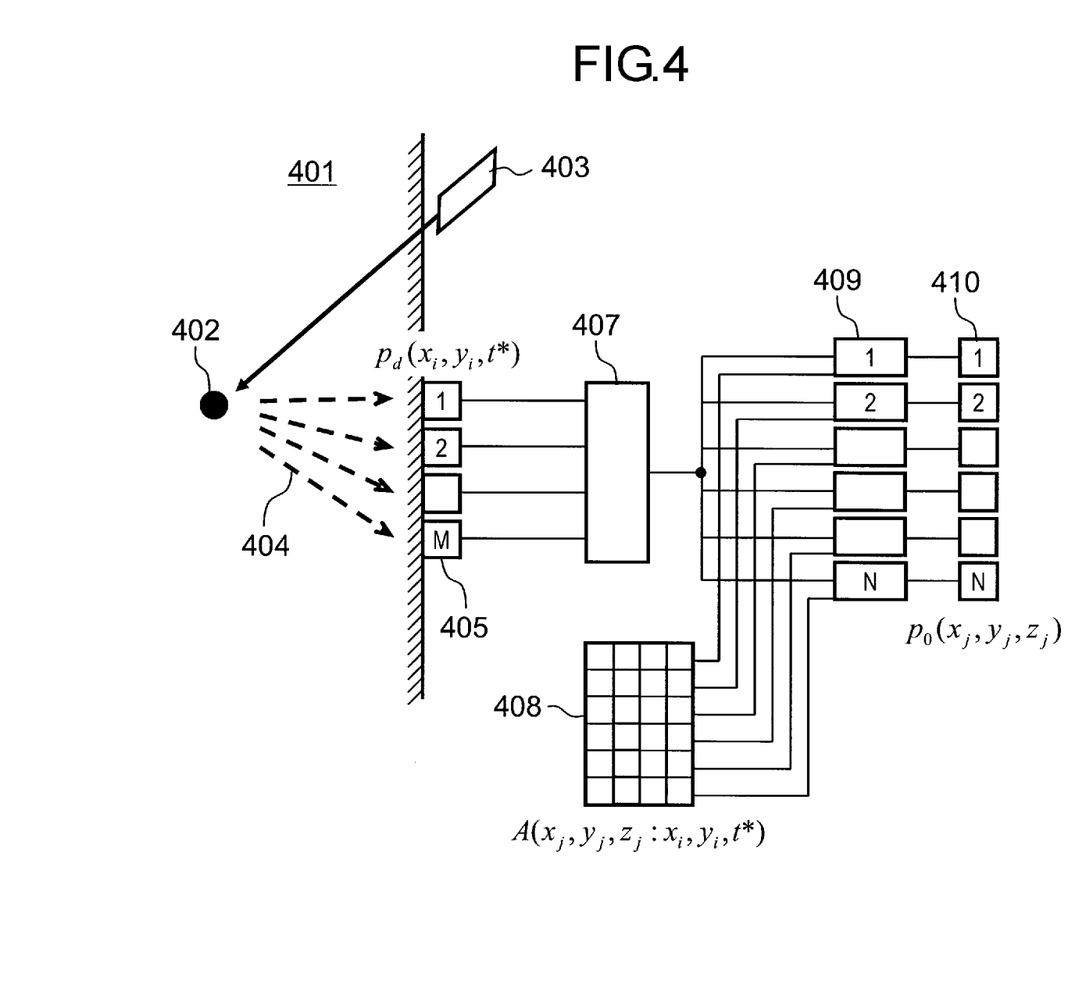
FIG. 4 is a diagram depicting a system configuration according to a first embodiment of the present invention.

Step 701: Select, using the selection unit (407), one acoustic transducer (405) i, receive an acoustic wave, and output the received signal $p_d(x_i,y_i,t^*)$.

Step 702: Read N number of coefficients $A(x_j,y_j,z_j;x_i,y_i,t^*)$ corresponding to each region j (j=0, 1, . . . , N) in the "acoustic transducer i, time t*" from the coefficient memory (408), and multiply $p_d(x_i,y_i,t^*)$ by each coefficient A respectively using N number of multiplier units (409). These N number of processings are executed simultaneously (in parallel).

Step 703: Accumulate (add) the N number of multiplication results $A(x_j,y_j,z_j;x_i,y_i,t^*) \cdot p_d(x_i,y_i,t^*)$ in the N number of voxel memories (410) respectively. These N number of processings are also executed simultaneously (in parallel).

Step 704: Sequentially select M number of acoustic transducers i and repeat the processings in Steps 701 to 703. As a result, the instantaneous value of the initial pressure $p_0$ at time t*, that is $\iint A(x_j,y_j,z_j;x_i,y_i,t^*) \cdot p_d(x_i,y_i,t^*) dx_i dy_i$ is stored in each voxel memory (410).

Step 705: Repeat the processings in Steps 701 to 704 for the entire period of receiving acoustic waves from each region, whereby the value of the initial pressure $P_0(x_j,y_j,z)$ of each region j expressed by Eq. (103) is accumulated in each voxel memory (410). Thus three-dimensional image data on the interior of a subject is generated.

(Algorithm 2)

Figure 2:
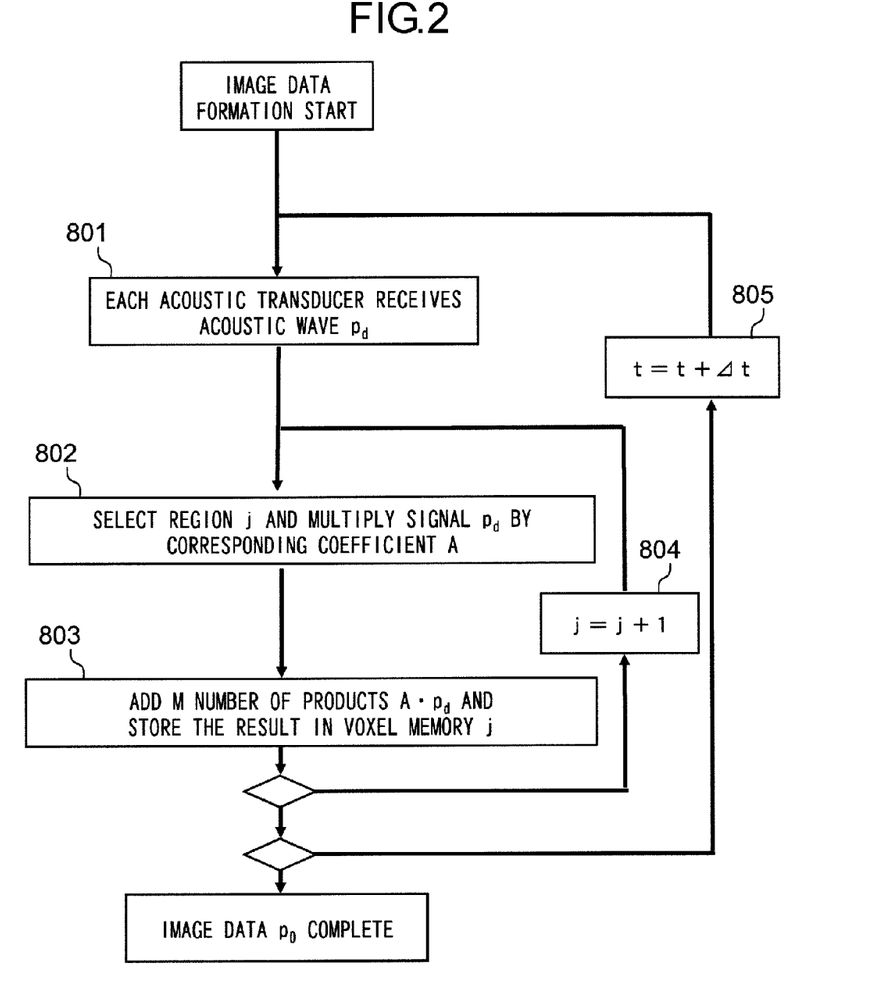
FIG. 2 is a flow chart depicting a computing algorithm 2 of the present invention.

FIG. 2 shows another example of an algorithm for generating image data. While algorithm 1 in FIG. 1 is for executing, in parallel, the processings for determining the respective values of the N number of regions from the received signal from one acoustic transducer, algorithm 2 in FIG. 2 is for executing, in parallel, the processings for determining a value of one region from the respective received signals from M number of acoustic transducers. In the following description, a number in ( ) is a number assigned to a composing element of the device shown in FIG. 6, which is described later. In the coefficient memory (609), coefficients A corresponding to all the pre-computed combinations of i, j and t* are stored. It is assumed that the voxel memory (612), variables t, j or the like have been initialized before Step 801.

Figure 6:
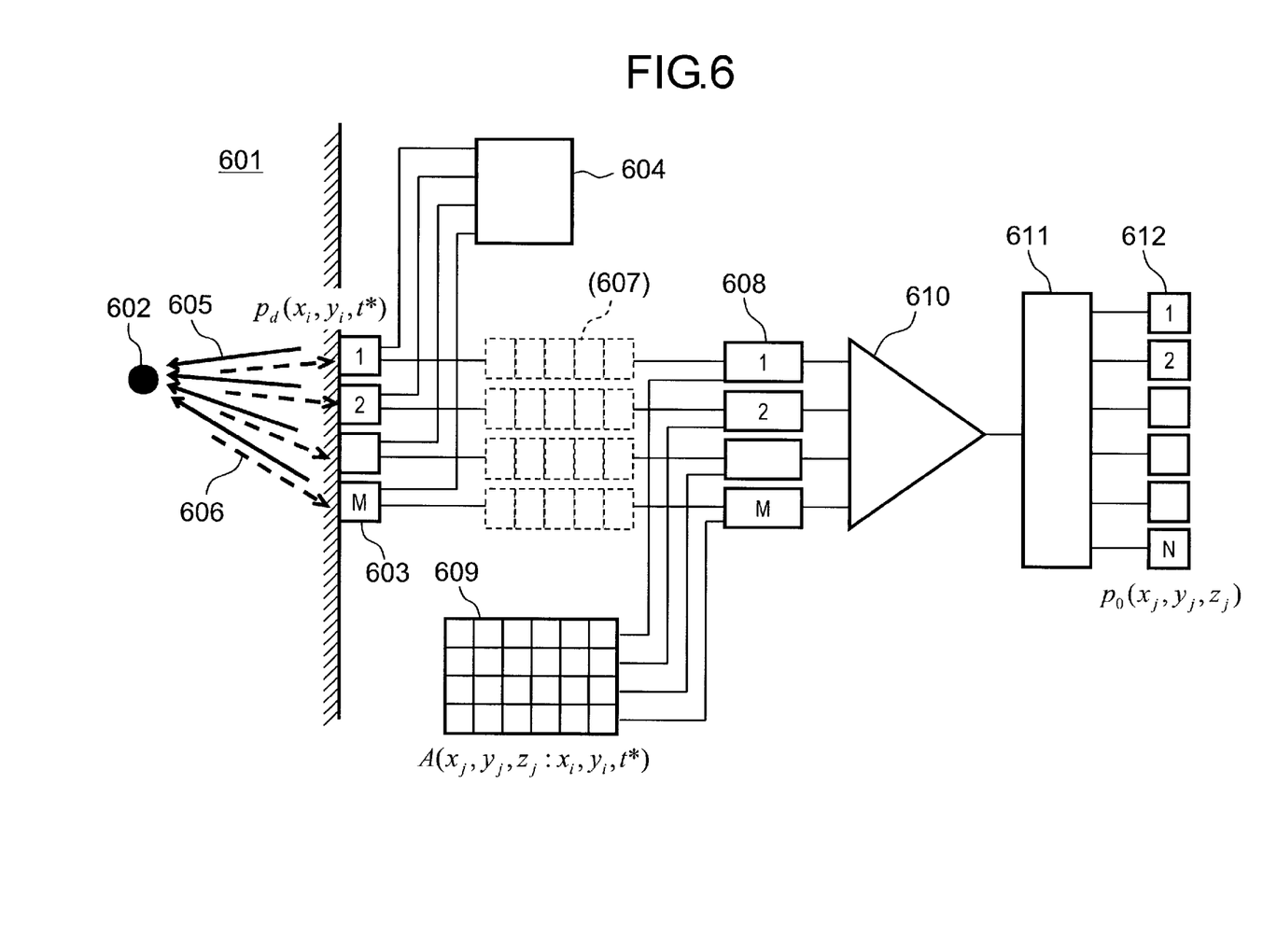
FIG. 6 is a diagram depicting a system configuration according to a third embodiment of the present invention.

Step 801: Receive the respective acoustic waves by M number of acoustic transducers (603), and output the received signal $p_d(x_i,y_i,t^*)$.

Step 802: Select region j and read M number of coefficients $A(x_j,y_j,z_j;x_i,y_i,t^*)$ corresponding to each acoustic transducer i (i=0, 1, . . . , M) in "region j, time t*" from the coefficient memory (609). Multiply the corresponding received signals $p_d(x_i,y_i,t^*)$ by the coefficient A respectively using the M number of multiplier units (608). These M number of processings are executed simultaneously (in parallel).

Step 803: Add M number of multiplication results $A(x_j,y_j,z_j;x_i,y_i,t^*) \cdot p_d(x_i,y_i,t^*)$ using the accumulation unit (610), and accumulate (add) the result in the voxel memory (612) corresponding to the region j using the selection unit (611).

Step 804: Sequentially select N number of regions j and repeat the processings in Steps 802 and 803. As a result, the instantaneous value of the initial pressure $p_0$ at time t*, that is $\iint A(x_j,y_j,z_j,x_i,y_i,t^*) \cdot p_d(x_i,y_i,t^*) dx_i dy_i$, is stored in each voxel memory (612).

Step 805: Repeat the processings in Steps 801 to 804 for the entire period of receiving acoustic waves from each region, whereby the value of the initial pressure $p_0(x_j,y_j,z_j)$ of each region j expressed by Eq. (103) is accumulated in each voxel memory (612). In this way three-dimensional image data on the interior of a subject is generated.

(Algorithm 3)

Figure 3:
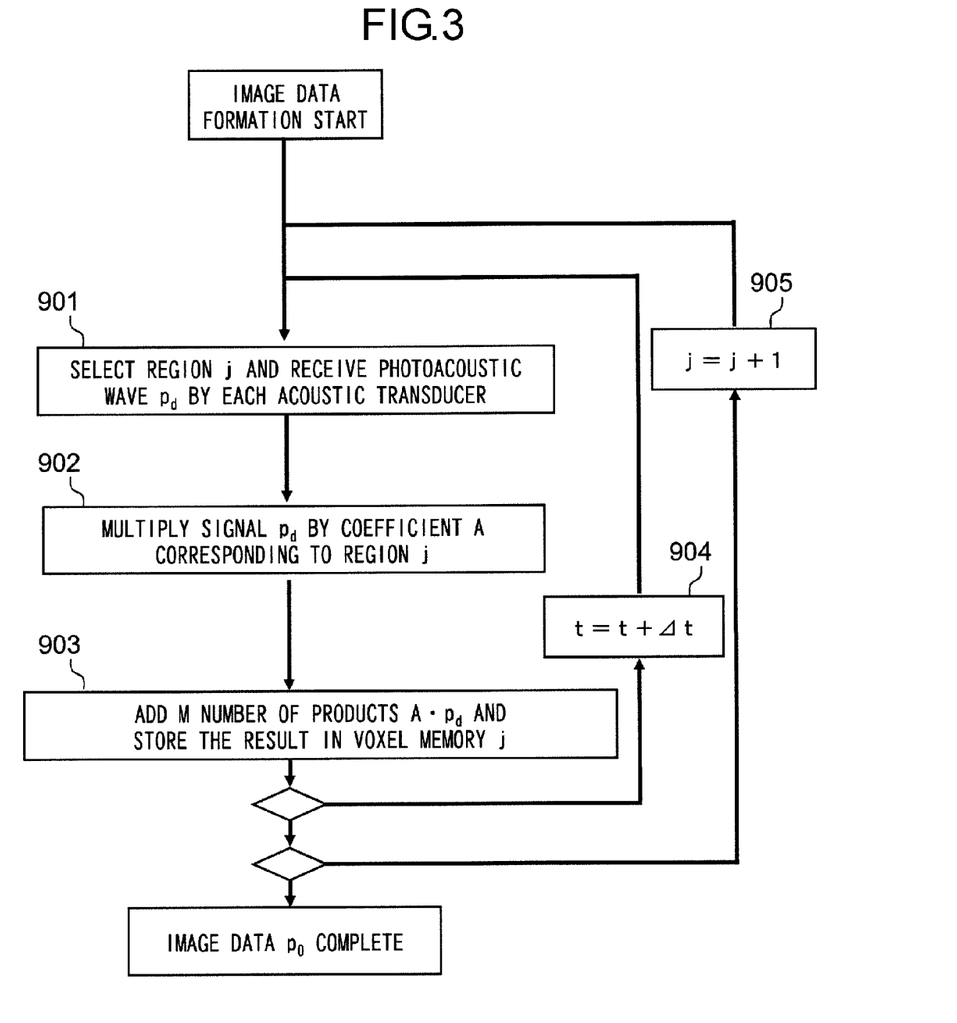
FIG. 3 is a flow chart depicting a computing algorithm 3 of the present invention.

FIG. 3 shows another example of an algorithm for generating image data. In the above mentioned algorithms 1 and 2, instantaneous values of the pressure $p_0$ of all the regions are calculated for each time step Δt, but in algorithm 3 in FIG. 3, the processing for determining the value of the initial pressure $p_0$ from the received signals in an entire period is sequentially executed for each region. This algorithm can preferably be applied to an ultrasonic echo apparatus which performs transmission beam focus. In the following description, a number in ( ) is a number assigned to a composing element of the apparatus shown in FIG. 6, which is described later. In the coefficient memory (609), coefficients A corresponding to all the pre-computed combinations of i, j and t* are stored. It is assumed that the voxel memory (612), variables t, j or the like, have been initialized before Step 901.

Step 901: Receive respective acoustic waves by M number of acoustic transducers (603), and output the received signal $p_d(x_i,y_i,t^*)$.

Step 902: Select region j and read M number of coefficients $A(x_j,y_j,z_j:x_i,y_i,t^*)$ corresponding to each acoustic transducer i (i=0, 1, . . . , M) in "region j, time t*" from the coefficient memory (609). Multiply corresponding signals $p_d(x_i,y_i,t^*)$ by the coefficient A respectively using the M number of multiplier units (608). If the transmission beam focus is performed, the region j located at the focal point of the transmitted acoustic wave is selected. These M number of processings are executed simultaneously (in parallel).

Step 903: Add M number of multiplication results A ($x_i,y_i,z_i:x_i,y_i,t^*$)·$p_d(x_i,y_i,t^*)$ using the accumulation unit (610), and accumulate (add) the result in a voxel memory j (612) corresponding to the region j using the selection unit (611).

Step 904: Repeat the processings in Steps 901 to 903 for the entire period of receiving the signals from the region j. As a result, the value of the initial pressure $p_0(x_j,y_j,z_j)$ of the region j expressed by Eq. (103) is accumulated in the voxel memory j corresponding to the region j.

Step 905: Repeat the processings in Steps 901 to 904 for all the regions j (that is, while transmitting acoustic waves so as to focus on each region j), whereby three-dimensional image data o the interior of a subject is generated in the voxel memory (612).

Generally in the case of an ultrasonic echo apparatus, ultrasonic waves are transmitted so as to sequentially focus on each region j, and sequentially process reflected waves reflected from the region j in order to enhance signal intensity. According to algorithm 3 shown in FIG. 3, this sequence can be executed by the apparatus in FIG. 6. Hence one apparatus confirmation shown in FIG. 6 can be used for both the generation of the ultrasonic echo image (algorithm 3 in FIG. 3) and the generation of the PAT image (algorithm 2 in FIG. 2).

(Advantage of these Algorithms)

A number of times of multiplication required for each of the above mentioned algorithms 1 to 3 is roughly estimated. It is assumed that the coefficients A have been computed and stored in the coefficient memory in advance. In the case of algorithm 1, the N number of times of multiplication in Step 702 is repeated M number of times in the loop of Step 704, and is then repeated T number of times in the loop of Step 705. As a result, the number of times of multiplication is N×M×T times, and if it is set that N=$L^3$, T×M≈$L^3$, as mentioned above, then approximately $L^6$ times of multiplication is required. In the same manner, in the case of algorithm 2, M number of times of multiplication in Step 802 is repeated N number of times in the loop of Step 804, and is then repeated T number of times in the loop of Step 805, so the number of times of multiplication is M×N×T≈$L^6$ times. In the case of algorithm 3, M number of times of multiplication in Step 902 is repeated T number of times in the loop of Step 904, and then is repeated N number of times in the loop of Step 905, so the number of times of multiplication is M×T×N≈$L^6$ times.

The number of times of multiplication ($L^6$) is approximately half the number of times of the conventional Fourier-domain method ($2L^6$). Furthermore, noteworthy of this algorithm is that the processings in Steps 702, 802 and 902 are in such a form that can be easily processed in parallel. For example, if N number of times of multiplication in Step 702 are processed in parallel in algorithm 1, the number of computing steps is $L^3$. Also if M number of times of multiplication in Step 802 or 902 are processed in parallel in algorithm 2 or 3, then the number of computing steps is $L^4$. These numbers of steps are much less than the number of steps $L^4 \log^2(L)$ in the case of using a fast Fourier-transform in the conventional Fourier-domain method. Hence according to the present algorithm, image forming processing by the Fourier-domain method can be dramatically faster, and high resolution three-dimensional image data can be processed in real-time.

A position ($x_i,y_i$) of an acoustic transducer is determined by the structure of the probe, and coordinates ($x_j,y_j,z_j$) of a measurement region and measurement time step t* can also be determined in advance by selecting a pattern out of a plurality of patterns, according to the intended use and required resolution. As a consequence, the coefficient A can be computed in advance.

In the above description, it is assumed that the received signals $p_d(x_i,y_i,t^*)$ of the acoustic waves which arrived from the acoustic transducers are completely processed in real-time. However such a time as 100 microseconds until complete arrival of the acoustic waves from all regions is extremely short in a human sense, so output from each acoustic transducer i may be stored in a buffer memory once, so that the stored data is output and processed in the sequence of reception at an interval longer than the time of reception. In this case, even if the interval is extended to 1000 times, the processing is completed in 100 ms, which is perceived as almost real-time processing by human senses. On the other hand, signal processing (e.g. Steps 701 to 705) can have a 1000 times time-based margin. In this case, the content of the buffer memory can be read only once, and essentially there is no need to repeat.

To execute the above algorithms, it is possible that the capacity of the memory (coefficient memory) for storing the coefficients A becomes enormous. A number of coefficients A is T×M×N(≈$L^6$), so if 1000 data is obtained in one dimension (L=1000), and if one coefficient A is 4 bytes, then 4×$10^{18}$ bytes of memory capacity is required. However the capacity of the coefficient memory can be decreased by the following means.

Means 1) Eq. (104) of the coefficient A is symmetrical with respect to (u, v). Therefore if half of the plane generated by (u, v) is integrated, Eq. (104) can be determined by doubling the result.

Means 2) If the x, y array of the region, of which image data is generated, inside the subject, is matched with an x, y array of the acoustic transducers, these variables simply appear as relative values $(x_i-x_j)$ and $(y_i-y_j)$ in Eq. (104), so the $L^2$ number of coefficients A have a same value. In other words, by using one coefficient A for $L^2$ number of calculations having the same $(x_i-x_j)$ and $(y_i-y_j)$, the memory capacity can be decreased to $1/L^2$.

The case of the acoustic transducers arrayed on a plane was described above for simplification. But the present invention can be applied to the case of acoustic transducers arrayed not only on a plane but also along a curved surface.

Now in order to exhibit the effect of the present invention, a system configuration of an image forming apparatus and operation thereof, which are preferable modes for carrying out the invention, will be described. The following image forming apparatus is an apparatus which generates image data of the information on the interior of a subject based on acoustic waves irradiated from the interior of the subject, and is used for photoacoustic tomography (PAT) and ultrasonic echo diagnosis apparatuses. The image data generated by the image forming apparatus is displayed on a display unit (monitor), which is not illustrated, as a three-dimensional image.

Embodiment 1

FIG. 4 is a diagram depicting a system configuration of an image forming apparatus according to Embodiment 1. This embodiment is an example when the above mentioned algorithm 1 is applied to generating the image data in photoacoustic tomography (PAT). This system has an electromagnetic wave pulse source 403, an acoustic probe having M number of acoustic transducers 405, and an image processing unit which determines the intensity of a photoacoustic wave irradiated from each region inside an subject, based on the received signals of photoacoustic waves which are received by the acoustic transducer 405 for a predetermined period. The image processing unit of the present embodiment has a selection unit 407, a coefficient memory 408, N number of multiplier units 409, and N number of voxel memories 410. Using this system, the initial pressure of N number of regions j 402 inside the subject 401 is determined, and three-dimensional image data is generated.

The electromagnetic wave pulse source 403 is an electromagnetic wave pulse irradiation unit which irradiates pulses of visible light, near-infrared light of which wavelength is about 700 to 1160 nm, and micro-wave of which frequency is 2.45 GHz, at a pulse width several nanoseconds to several tens of nanoseconds. When this pulse is irradiated onto the subject 401 and a part of the energy is absorbed by region j, photoacoustic waves 404 are irradiated from the region j by the photoacoustic effect. The photoacoustic waves 404 are converted into electric signals (received signals) by the M number of photoacoustic transducers 405. In FIG. 4, the acoustic transducers 405 are depicted as if arrayed one-dimensionally, but actually the acoustic transducers 405 are arrayed two-dimensionally. A pre-amplifier may be connected to each acoustic transducer although this is not illustrated. An A/D conversion unit may be connected to each acoustic transducer. A sample hold unit may also be connected to each acoustic transducer. Hereafter an acoustic transducer including these units is also simply referred to as an "acoustic transducer".

Output of each acoustic transducer 405 is connected to the selection unit 407. At a certain time t*, the selection unit 407 selects an i-th acoustic transducer out of the M number of acoustic transducers 405, and outputs the output thereof, that is the received signal $p_d(x_i,y_i,t^*)$, to all the N number of multiplier units 409, corresponding to the N number of regions 402 simultaneously. Synchronizing with this, coefficient $A(x_j,y_j,z_j:x_i,y_i,t^*)$ is read to the j-th multiplier unit 409 from the coefficient memory 408. The multiplier unit 409 calculates the product of the output $p_d$ of the acoustic transducer 405 and the coefficient A, that is A $(x_j, y_j,z_j:x_i, y_i, t^*) \cdot p_d (x_i,y_i,t^*)$. This result is stored in a voxel memory 410 corresponding to each multiplier unit. Output of M number of acoustic transducers 405 is sequentially processed, and $\iint A (x_j,y_j,z_j:x_i,y_i,t^*) \cdot p_d(x_i,y_i,t^*)dx_i dy_i$ at time t* is computed. Then the $p_d(x_i,y_i,t^*+\Delta t^*)$ signal of the acoustic transducers at the next time $t^*+\Delta t^*$ is processed in a same manner. By repeating the above processing for a predetermined period, the initial sound pressure $p_0(x_j,y_j,z_j)$ expressed by Eq. (103) is obtained for all the voxels.

According to the present embodiment, N number of multiplication can be processed in parallel, so the number of computing steps becomes $M \times T(=L^3)$ times. Compared with the case of performing the same computing by the conventional Fourier-domain method, which requires $L^6$ steps, computing time is dramatically decreased by the configuration of the present embodiment.

Embodiment 2

Figure 5:
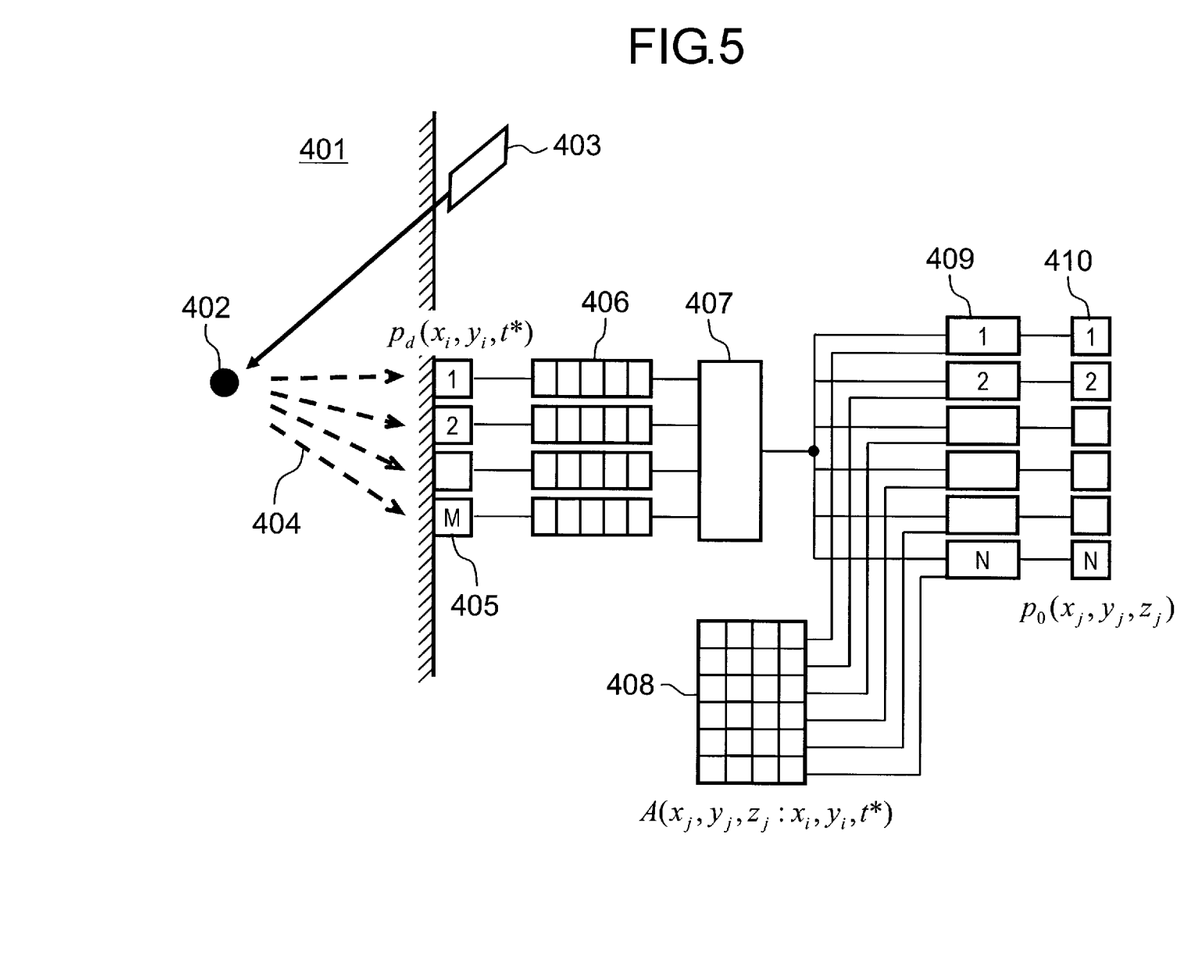
FIG. 5 is a diagram depicting a system configuration according to a second embodiment of the present invention.

FIG. 5 is a diagram depicting a system configuration according to Embodiment 2. The system of the present embodiment has a line memory 406 for buffering an output signal of the acoustic transducer 405 between the acoustic transducer 405 and the selection unit 407. The other composing elements, which are the same as those in Embodiment 1, are denoted with the same reference numerals as FIG. 4.

The line memory 406 is an FIFO memory, for sequentially storing received signals which are output from each acoustic transducer 405, and outputting the stored received signals to the selection unit 407 in the sequence of reception (input). The functions after the selection unit 407 are the same as Embodiment 1. The interval of the line memory 406, which outputs signals, can be set appropriately. By setting the second interval of outputting signals from the line memory 406 to be longer than the first interval of storing the signals in the line memory 406, the operation clock of the image processing unit (e.g. multiplier unit 409) can be slower than Embodiment 1.

Normally it takes about 100 microseconds for an acoustic wave to arrive from a deeper region in a subject. If a received signal is obtained at every 1 microsecond for 100 microseconds, 100 signals are stored in the line memory 406. Even if these signals are read at 1000 times interval, it takes only about 100 milliseconds to output all the signals from the line memory 406. Such time is perceived by human senses as a real-time operation. If the interval of outputting signals is increased like this, such processings as scanning, reading of a coefficient, multiplication and writing to a voxel memory by the selection unit 407 can be performed with an extra margin. This is an advantage when designing circuits.

Embodiment 3

FIG. 6 is a diagram depicting a system configuration according to Embodiment 3. The present embodiment is an example of applying the above mentioned algorithm 3 to generate image data of an ultrasonic echo. This system has a transmission circuit 604, an acoustic probe having M number of acoustic transducers 603, M number of multiplier units 608, a coefficient memory 609, an accumulation unit 610, a selection unit 611, and N number of voxel memories 612. As the broken lines show, a line memory 607 may be inserted between the acoustic transducer 603 and the multiplier unit 608 if necessary, so as to execute the same processing as Embodiment 2.

The acoustic waves (ultrasonic waves) are transmitted from the acoustic transducer 603 to the region j 602 in the subject 601. The acoustic transducer 603, using a piezoelectric element and capacitive coupling, can be used not only for receiving acoustic waves, but also for transmission. The configuration is not limited to that in FIG. 6, but an ultrasonic transmission unit may be disposed separately from the acoustic transducer 603. A transmission signal, which is appropriately delayed, is sent to an individual acoustic transducer 603 (or ultrasonic transmission unit) by the transmission circuit 604, and as a result, the ultrasonic wave which converges on the rejoin j is transmitted. If the region j has an acoustic characteristic that is different from the peripheral tissue, an ultrasonic wave having an intensity according to the difference is reflected and received by the acoustic transducer 603.

The output $p_d(x_i,y_i,t^*)$ of the acoustic transducer 603 or the line memory 607 at time $t^*$ is input to the multiplier unit 608 according to each acoustic transducer 603. In each multiplier unit 608, a coefficient A corresponding to the region j is read from the coefficient memory 609. The multiplier unit 608 calculates the product of the output $p_d$ of the acoustic transducer 603 and the coefficient A, that is, $A(x_j,y_j,z_j:x_i,y_i,t^*) \cdot p_d(x_i,y_i,t^*)$. The outputs of the M number of multiplier units 608 are added by the accumulation unit 610, and $\iint A(x_j,y_j,z_j:x_i,y_i,t^*) \cdot p_d(x_i,y_i,t^*) dx_i dy_i$ is determined. This is added to the voxel memory 612 corresponding to the region j via the selection unit 611. If this processing is repeated for a predetermined period, the reflection intensity $p_0(x_j,y_j,z_j)$ with respect to the region j expressed by Eg. (103) is obtained. Then the ultrasonic wave is transmitted so as to converge on another region j', and the above processing is performed so as to obtain the reflection intensity of the region j'. By performing this processing for all the regions, distribution of the ultrasonic reflection intensity in the interior of a subject can be generated into image data.

According to the present embodiment, M number of multiplications can be processed in parallel, so the number of computing steps becomes $N \times T(=L^4)$ times. Compared with the case of performing the same computing by the conventional Fourier-domain method, which requires $L^6$ steps, computing time is dramatically decreased by the configuration of the present embodiment.

The system configuration of the present embodiment can also be applied to PAT. In this case, it is preferable to use the above mentioned algorithm 2, and scan the region j at each time $t^*$. In this case as well, image data can be generated by a number of computing steps ($L^4$), that is, much less than the conventional Fourier-domain method.

Another advantage of this embodiment is that image data of PAT and that of ultrasonic echo can be generated using a same system configuration. For example, if an image of PAT and an image of ultrasonic echo can be superimposed on a display, more detailed information on the state of the interior of a subject can be obtained.

In the above embodiments, the multiplier unit, accumulation unit, selection unit, coefficient memory, voxel memory or the like, is constituted by a dedicated circuit, but these functions and processings can also be implemented by software (programs) of a computer. In other words, the functions of the coefficient memory and the voxel memory are played by the storage apparatus (memory) of a computer, and such processings as multiplication, addition and selection of the digital signals received from the acoustic transducers are performed by programs. In concrete terms, the above mentioned functions and processings are implemented by supplying software (programs) for implementing the functions of the above embodiments to a system or an apparatus via a network or various storage media, and having the computer (or CPU or MPU) of the system or apparatus read and execute the programs. In this case, computing time can be dramatically decreased by using a CPU, which can execute parallel processing, or by performing parallel processing using a plurality of CPUs.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., non-transitory computer-readable medium).

This application claims the benefit of Japanese Patent Application No. 2009-261898, filed on Nov. 17, 2009, Japanese Patent Application No. 2010-196429, filed on Sep. 2, 2010, and Japanese Patent Application No. 2010-245390, filed on Nov. 1, 2010, which are hereby incorporated by reference herein in their entirety.

The invention claimed is:

1. An image forming apparatus for creating image data from information on an interior of a subject based on acoustic waves irradiated from the interior of the subject, comprising:
   a plurality of acoustic transducers which receive acoustic waves and convert the acoustic waves into received signals; and
   an image processing unit which obtains intensity of acoustic waves irradiated from a plurality of regions inside the subject respectively by processing the received signals, which are output from said plurality of acoustic transducers, wherein said image processing unit includes:
      a coefficient memory which stores coefficients determined by a position of a corresponding acoustic transducer, a position of a region a time of receipt of the acoustic wave, and variables of a Fourier transform having wave number dimensions;
      a multiplier unit which obtains a coefficient corresponding to the acoustic transducer from said coefficient memory, and multiplies a received signal which is output from the acoustic transducer by the coefficient, for each acoustic transducer; and
      a voxel memory which accumulates multiplication results of said multiplier unit for each region,
   wherein a coefficient A is obtained by a following formula, when $(x_i,y_i)$ represents a position of the acoustic transducer i, $(x_j,y_j,z_j)$ represents a position of a region j in the subject, and t* represents a time of receipt of the acoustic wave:

$$A(x_j, y_j, z_j: x_i, y_i, t^*) = \quad \text{[Expression 1]}$$

$$\frac{1}{(2\pi)^3} \int\int\int_{-\infty}^{\infty} \frac{2w \operatorname{sgn}(w)}{\sqrt{u^2+v^2+w^2}} \exp\left\{i\left[\begin{array}{c} u(x_i-x_j)+v(y_i-y_j)-wz_j+\\ \operatorname{sgn}(w)\sqrt{u^2+v^2+w^2}\, t^* \end{array}\right]\right\} du\, dv\, dw$$

where u, v and w are variables of a Fourier transform, and sgn(w) is a function which is 1 when w>0, is 0 when w=0, and is −1 when w<0.

2. The image forming apparatus according to claim 1, wherein said multiplier unit comprises a plurality of multiplier units which correspond to respective ones of the plurality of regions, and wherein said plurality of multiplier units execute, in parallel, processing for multiplying a received signal output from one acoustic transducer by a coefficient which corresponds to each of the plurality of regions respectively.

3. The image forming apparatus according to claim 1, wherein said multiplier unit comprises a plurality of multiplier units which correspond to respective ones of the plurality of acoustic transducers, and wherein said plurality of multiplier units execute, in parallel, processing for multiplying the received signals which are output from the plurality of acoustic transducers by a coefficient which corresponds to one region respectively.

4. The image forming apparatus according to claim 1, further comprising:
a buffer memory, which is provided between said acoustic transducers and said image processing unit, and sequentially stores the received signals which are output from the plurality of acoustic transducers and outputs stored received signals to said image processing unit in a sequence of reception.

5. The image forming apparatus according to claim 4, wherein said buffer memory stores the received signals output from said plurality of acoustic transducers at a first time interval, and outputs stored received signals to said image processing unit at a second time interval, which is longer than the first time interval.

6. The image forming apparatus according to claim 1, further comprising:
an electromagnetic wave pulse irradiation unit for irradiating the subject with an electromagnetic wave pulse,
wherein said acoustic transducers receive a photoacoustic wave irradiated by a photoacoustic effect from a region which has absorbed energy of an irradiated electromagnetic wave pulse.

7. The image forming apparatus according to claim 1, wherein said acoustic transducer transmits an ultrasonic wave to the subject and receives a reflected wave of a transmitted ultrasonic wave.

8. An image forming method for receiving acoustic waves irradiated from a plurality of regions inside a subject for a predetermined period using a plurality of acoustic transducers, converting the acoustic waves into received signals, and processing the received signals to create image data of intensity of the acoustic waves irradiated from the regions, comprising the steps of:
storing coefficients determined by a position of the acoustic transducer, a position of a region, a time of receipt of the acoustic wave, and variables of a Fourier transform having wave number dimensions;
obtaining a coefficient corresponding to the received signal of the one acoustic transducer from the coefficient memory;
multiplying the received signal by the coefficient; and
accumulating results of multiplying the received signal by the coefficient in a voxel memory for each region,
wherein a coefficient A is obtained by a following formula, when $(x_i,y_i)$ represents a position of the acoustic transducer i, $(x_j,y_j,z_j)$ represents a position of a region j in the subject, and t* represents a time of receipt of the acoustic wave:

$$A(x_j, y_j, z_j: x_i, y_i, t^*) = \quad \text{[Expression 1]}$$

$$\frac{1}{(2\pi)^3} \int\int\int_{-\infty}^{\infty} \frac{2w \operatorname{sgn}(w)}{\sqrt{u^2+v^2+w^2}} \exp\left\{i\left[\begin{array}{c} u(x_i-x_j)+v(y_i-y_j)-wz_j+\\ \operatorname{sgn}(w)\sqrt{u^2+v^2+w^2}\, t^* \end{array}\right]\right\} du\, dv\, dw$$

where u, v and w are variables of a Fourier transform, and sgn(w) is a function which is 1 when w>0, is 0 when w=0, and is −1 when w<0.

9. A non-transitory computer readable medium which stores a program for causing a computer to execute the steps of the image forming method according to claim 8.

10. The image forming apparatus according to claim 1, further comprising:
a memory which stores the received signals which are output from said plurality of acoustic transducers,
wherein the image processing unit obtains intensity of acoustic waves irradiated from the plurality of regions inside the subject respectively by processing the received signals stored in said memory.

11. The image forming apparatus according to claim 10, further comprising:
a selection unit which selects a region, selects a signal corresponding to a selected region from the received signals stored in the memory, and selects a coefficient corresponding to the selected region from the coefficients stored in the coefficient memory,
wherein the multiplier unit multiplies a selected signal by a selected coefficient; and
wherein the voxel memory accumulates multiplication results of said multiplier unit for each region.

* * * * *